United States Patent
Shibata et al.

(10) Patent No.: US 9,857,346 B2
(45) Date of Patent: Jan. 2, 2018

(54) UREA WATER SUPPLY GUIDANCE OUTPUT DEVICE FOR WORKING VEHICLE AND METHOD OF OUTPUTTING UREA WATER SUPPLY GUIDANCE OF WORKING VEHICLE

(71) Applicant: Komatsu Ltd., Tokyo (JP)

(72) Inventors: Takehiro Shibata, Oiso-machi (JP); Tsuyoshi Tanaka, Fujisawa (JP)

(73) Assignee: Komatsu Ltd., Tokyo (JP)

( * ) Notice: Subject to any disclaimer, the term of this patent is extended or adjusted under 35 U.S.C. 154(b) by 722 days.

(21) Appl. No.: 14/370,847

(22) PCT Filed: Feb. 28, 2014

(86) PCT No.: PCT/JP2014/055190
§ 371 (c)(1),
(2) Date: Jul. 7, 2014

(87) PCT Pub. No.: WO2015/025543
PCT Pub. Date: Feb. 26, 2015

(65) Prior Publication Data
US 2015/0268212 A1    Sep. 24, 2015

(51) Int. Cl.
*G01N 33/18* (2006.01)
*E02F 9/26* (2006.01)
(Continued)

(52) U.S. Cl.
CPC .............. *G01N 33/18* (2013.01); *E02F 9/26* (2013.01); *F01N 3/0807* (2013.01); *F01N 11/00* (2013.01);
(Continued)

(58) Field of Classification Search
USPC .......................................................... 702/50
See application file for complete search history.

(56) References Cited

U.S. PATENT DOCUMENTS 7,946,109 B2    5/2011    Potter et al.
8,626,405 B2    1/2014    Stickel et al.
(Continued)

FOREIGN PATENT DOCUMENTS

CN            102971169 A        3/2013
DE    10 2007 059 473 A1        6/2008
(Continued)

OTHER PUBLICATIONS

International Search Report and Written Opinion dated May 20, 2014, issued for PCT/JP2014/055190.

*Primary Examiner* — Paul D Lee
(74) *Attorney, Agent, or Firm* — Locke Lord LLP

(57) ABSTRACT

A urea water supply guidance output device for a working vehicle includes: a urea water residual amount detection unit configured to detect a urea water residual amount in a urea water tank; an operation time measurement unit configured to measure an operation time of the working vehicle; a unit urea water consumption amount calculation unit configured to calculate a unit urea water consumption amount for each predetermined unit operation time; a urea water remaining time calculation unit configured to calculate an average urea water consumption amount and to calculate a urea water remaining time indicating a time to generation of urea water supply alarm; and an output processing unit configured to output guidance including the urea water remaining time when the urea water remaining time is a predetermined time or less.

9 Claims, 6 Drawing Sheets

(51) Int. Cl.
  *F01N 11/00* (2006.01)
  *F01N 3/08* (2006.01)
  *F02D 41/22* (2006.01)

(52) U.S. Cl.
  CPC ...... *F01N 2550/05* (2013.01); *F01N 2610/02* (2013.01); *F01N 2900/1814* (2013.01); *F02D 2041/228* (2013.01); *Y02T 10/47* (2013.01)

(56) References Cited

U.S. PATENT DOCUMENTS

| | | | |
|---|---|---|---|
| 2007/0204677 A1* | 9/2007 | Nishina | F01N 3/2066 73/53.01 |
| 2008/0141659 A1 | 6/2008 | Potter et al. | |
| 2008/0306673 A1* | 12/2008 | Yasui | F01N 3/208 701/102 |
| 2012/0010786 A1 | 1/2012 | Stickel et al. | |
| 2013/0173106 A1 | 7/2013 | Konishi | |
| 2013/0255233 A1* | 10/2013 | Yasui | F01N 3/10 60/286 |
| 2014/0182274 A1* | 7/2014 | Toukairin | F01N 3/208 60/287 |

FOREIGN PATENT DOCUMENTS

| | | |
|---|---|---|
| DE | 10 2010 026 600 A1 | 1/2012 |
| JP | 2006-292418 A | 10/2006 |
| JP | 2008-163674 A | 7/2008 |
| JP | 2009-002859 A | 1/2009 |
| JP | 2009-121256 A | 6/2009 |
| JP | 2009-127521 A | 6/2009 |
| JP | 2010-166878 A | 8/2010 |
| JP | 2010-242692 A | 10/2010 |
| WO | WO-2009/001195 A1 | 12/2008 |
| WO | WO-2012/014845 A1 | 2/2012 |

* cited by examiner ical Problem

UREA WATER SUPPLY GUIDANCE OUTPUT DEVICE FOR WORKING VEHICLE AND METHOD OF OUTPUTTING UREA WATER SUPPLY GUIDANCE OF WORKING VEHICLE

FIELD

The present invention relates to a urea water supply guidance output device for a working vehicle and a method of outputting urea water supply guidance for a working vehicle capable of outputting guidance of information related to urea water supply that can be easily recognized by an operator.

BACKGROUND

Conventionally, exhaust gas purification devices for construction machines, which purify an exhaust gas discharged from an engine by injecting urea water accumulated in a urea water tank to an exhaust passage are known. Here, Patent Literature 1 discloses a technology in which, when a residual amount of the urea water becomes smaller than 5 L, the fact that the residual amount becomes smaller and a warning that urges supply of the urea water are displayed, and when the residual amount of the urea water becomes smaller than 3 L, a warning that operation restriction control of an engine and a hydraulic system is to be executed is displayed.

CITATION LIST

Patent Literature

Patent Literature 1: Japanese Patent Application Laid-open No. 2009-127521

SUMMARY

Technical Problem

By the way, an exhaust gas post-processing device for a working vehicle disclosed in Patent Literature 1 displays a urea water residual amount. However, a warning that urges supply of the urea water is displayed after the residual amount of the urea water becomes small, and thus arrangement and supply of the urea water cannot be performed in advance in a planned manner. Therefore, a urea water consumption amount so far in association with an operation of a working vehicle is obtained, and a future urea water consumption amount is predicted, whereby information related to urea water supply, for example, a time of alarm generation can be presented to an operator. However, when there has been a specific phenomenon, such as discharge or supply of the urea water, if the urea water consumption amount so far is obtained without considering the specific phenomenon, an obtained past urea water consumption amount cannot be the urea water consumption amount associated with an operation of a working vehicle, and an accurate time of the alarm generation is not presented to the operator.

The present invention has been made in view of the foregoing, and an objective is to provide a urea water supply guidance output device for a working vehicle and a method of outputting urea water supply guidance for a working vehicle, which can output, to the operator, guidance of accurate information related to a time of alarm generation issued due to a decrease in the urea water.

Solution to Problem

To solve the above-described problem and achieve the object, a urea water supply guidance output device for a working vehicle according to the present invention is a urea water supply guidance output device for a working vehicle configured to perform exhaust gas processing using urea water in a urea water tank and includes: a urea water residual amount detection unit configured to detect a urea water residual amount in the urea water tank; an operation time measurement unit configured to measure an operation time of the working vehicle; a unit urea water consumption amount calculation unit configured to calculate a unit urea water consumption amount for each predetermined unit operation time based on the urea water residual amount; a urea water remaining time calculation unit configured to calculate an average urea water consumption amount based on a unit urea water consumption amount in a past predetermined operation time, excluding a unit urea water consumption amount calculated at occurrence of a specific phenomenon of the unit urea water consumption amount, and to calculate a urea water remaining time indicating a time to generation of urea water supply alarm based on the average urea water consumption amount and a current urea water residual amount; and an output processing unit configured to output guidance including the urea water remaining time when the urea water remaining time is a predetermined time or less.

Moreover, in the above-described urea water supply guidance output device for a working vehicle according to the present invention, the specific phenomenon is one of discharge of the urea water from the urea water tank, supply of the urea water to the urea water tank, and system abnormality.

Moreover, in the above-described urea water supply guidance output device for a working vehicle according to the present invention, the urea water remaining time is a time to execution of output restriction control of the working vehicle.

Moreover, the above-described urea water supply guidance output device for a working vehicle according to the present invention includes an input unit configured to input an instruction of non-display or re-display of the output of guidance of the urea water remaining time.

Moreover, in the above-described urea water supply guidance output device for a working vehicle according to the present invention, the output processing unit is configured to output the output of guidance including the urea water remaining time after key-on is performed.

Moreover, a urea water supply guidance output device for a working vehicle according to the present invention is a urea water supply guidance output device for a working vehicle configured to perform exhaust gas processing using urea water in a urea water tank and includes: a urea water residual amount detection unit configured to detect a urea water residual amount in the urea water tank; an operation time measurement unit configured to measure an operation time of the working vehicle; a unit urea water consumption amount calculation unit configured to calculate a unit urea water consumption amount for each predetermined unit operation time based on the urea water residual amount; a urea water remaining time calculation unit configured to calculate an average urea water consumption amount based on a unit urea water consumption amount in a past predetermined operation time, excluding a unit urea water consumption amount calculated at occurrence of a specific phenomenon of one of discharge of the urea water from the urea water tank, supply of the urea water to the urea water tank, and system abnormality, of the unit urea water consumption amount; and an output processing unit configured to output guidance including the urea water remaining time at least after key-on is performed when the urea water remaining time is a predetermined time or less.

Moreover, a method of outputting guidance of urea water supply for a working vehicle according to the present invention is a method of outputting guidance of urea water supply for a working vehicle configured to perform exhaust gas processing using urea water in a urea water tank and includes: detecting a urea water residual amount in the urea water tank; measuring an operation time of the working vehicle; calculating a unit urea water consumption amount for each predetermined unit operation time based on the urea water residual amount; calculating an average urea water consumption amount based on a unit urea water consumption amount in a past predetermined operation time, excluding a unit urea water consumption amount calculated at occurrence of a specific phenomenon of the unit urea water consumption amount, and calculating a urea water remaining time indicating a time to generation of urea water supply alarm based on the average urea water consumption amount and a current urea water residual amount; and outputting guidance including the urea water remaining time when the urea water remaining time is a predetermined time or less.

Moreover, in the above-described method of outputting guidance of urea water supply for a working vehicle according to the present invention, the specific phenomenon is one of discharge of the urea water from the urea water tank, supply of the urea water to the urea water tank, and system abnormality.

Moreover, in the above-described method of outputting guidance of urea water supply for a working vehicle according to the present invention, the urea water remaining time is a time to execution of output restriction control of the working vehicle.

Further, in the method of outputting urea water supply guidance for a working vehicle according to the present invention, the urea water remaining time is a time to execution of output restriction control of the working vehicle.

According to the present invention, a unit urea water consumption amount calculation unit calculates a unit urea water consumption amount for each predetermined unit operation time based on a urea water residual amount; a urea water remaining time calculation unit calculates an average urea water consumption amount based on a unit urea water consumption amount in a past predetermined operation time, excluding a unit urea water consumption amount calculated at occurrence of a specific phenomenon of the unit urea water consumption amount, and calculates a urea water remaining time indicating a time to generation of urea water supply alarm based on the average urea water consumption amount and a current urea water residual amount; and an output processing unit outputs guidance including the urea water remaining time when the urea water remaining time is a predetermined time or less. This enables the operator to accurately and reliably recognize the information related to the urea water supply.

BRIEF DESCRIPTION OF DRAWINGS

FIG. 4-1 is an explanatory diagram describing calculation of a urea water remaining time of when a specific phenomenon does not occur by a urea water remaining time calculation unit.

FIG. 4-2 is an explanatory diagram describing calculation of a urea water remaining time of when a specific phenomenon has occurred by a urea water remaining time calculation unit.

DESCRIPTION OF EMBODIMENTS

Hereinafter, embodiments of the present invention will be described with reference to the appended drawings.

Entire Configuration of Working Vehicle

Figure 1:
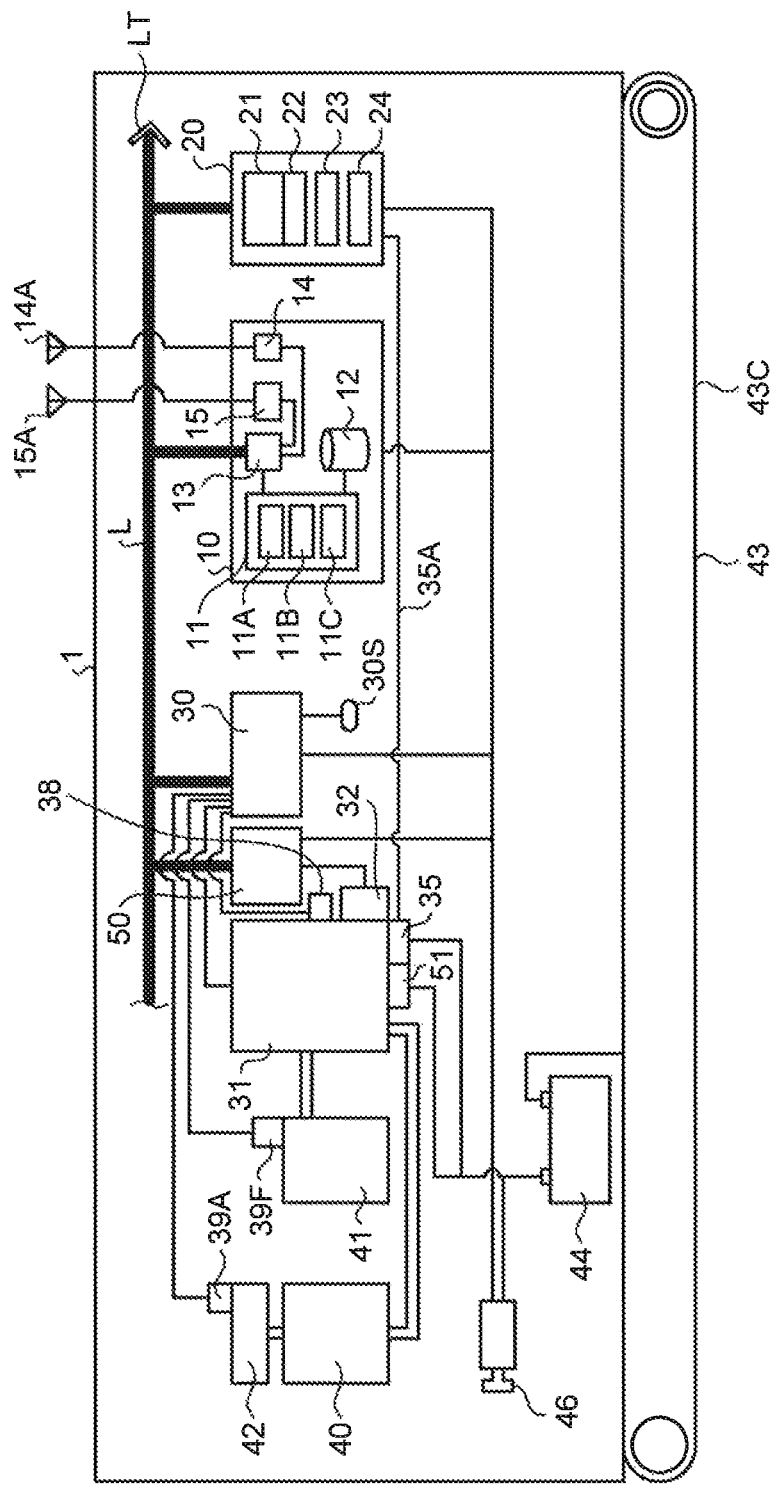
FIG. 1 is a block diagram illustrating an entire configuration of a working vehicle on which a urea water supply guidance output device for a working vehicle according to an embodiment of the present invention is mounted.

FIG. 1 is a block diagram illustrating an entire configuration of a working vehicle on which a urea water supply guidance output device for a working vehicle according to an embodiment of the present invention is mounted. A working vehicle 1 is an excavator, for example. The working vehicle 1 includes a processing device 10, a monitor 20, an engine controller 30 and a pump controller 50, and these units and devices are connected to an in-vehicle signal line L. Further, the working vehicle 1 includes an engine 31, a hydraulic pump 32, an alternator 35, a rotation speed detection sensor 38, a fuel tank 41, an exhaust gas processing device 40, a urea water tank 42, a storage battery 44, a key switch 46 and a starter 51.

The engine controller 30 controls the engine 31 and the exhaust gas processing device 40 that purifies an exhaust gas discharged from the engine 31. The engine 31 is a diesel engine. The exhaust gas processing device 40 purifies the exhaust gas using urea selective catalytic reduction (SCR), that is, urea water as a reducing agent. Therefore, the urea water for being supplied to the exhaust gas processing device 40 is accumulated in the urea water tank 42. As described above, the working vehicle 1 mounts an exhaust gas processing system including the exhaust gas processing device 40, the urea water tank 42, and the like.

Here, when a urea water residual amount accumulated in the urea water tank 42 is a predetermined residual amount or less, or when an error related to the exhaust gas processing system is detected, the engine controller 30 performs derate control that is output restriction control of the engine 31. The derate control is to restrict an output of the engine 31, and is to restrict an output of the engine 31 into a state of a low idle operation. Note that the derate control may restrict an output (absorption torque) of the hydraulic pump 32, or may restrict outputs of both of the engine 31 and the hydraulic pump 32. When performing the output restriction control of the engine 31 and the like, the engine controller 30 displays the fact of the control to the monitor 20.

Further, the engine controller 30 controls the amount of a fuel supplied to the engine 31 based on a rotation speed of a crank shaft of the engine 31 detected by the rotation speed detection sensor 38, the degree of opening of a fuel adjustment dial 30S, and the like. That is, the engine controller 30 controls an operation of the engine 31. The engine controller 30 controls the amount of the urea water supplied from the urea water tank 42 to the exhaust gas processing device 40 based on the amount of nitrogen oxides contained in the exhaust gas discharged from the engine 31, and the like. For example, the exhaust gas processing device 40 includes a sensor that detects the amount of nitrogen oxides contained in the exhaust gas, and if the nitrogen oxides detected by the sensor exceeds a predetermined amount, the exhaust gas processing device 40 supplies the urea water from the urea water tank 42 to an injection device (not illustrated), and the injection device injects the urea water into the exhaust gas. The nitrogen oxide contained in the exhaust gas is reduced to nitrogen and water.

Further, the engine controller 30 obtains a residual amount of a fuel of the fuel tank 41 based on a detection value of a liquid surface detection sensor 39F that detects the amount of a fuel accumulated in the fuel tank 41. The engine controller 30 transmits information indicating the obtained residual amount of a fuel to the monitor 20, and displays the residual amount of a fuel in a fuel level gauge, for example. The engine controller 30 obtains the residual amount of the urea water in the urea water tank 42 based on a detection value of a liquid surface detection sensor 39A that detects the amount of the urea water accumulated in the urea water tank 42. The engine controller 30 transmits the obtained residual amount of the urea water to the monitor 20, and the monitor 20 displays the residual amount of the urea water in a urea water level gauge. Note that a urea water residual amount detection unit 23 of the monitor 20 detects the residual amount of the urea water sent from the engine controller 30. Note that the liquid surface detection sensors 39F and 39A can use an ultrasonic sensor that can acquire a height of a liquid surface by detecting a float floating on a liquid, for example. Alternatively, an amount of the liquid can be detected using another detector, such as a liquid amount sensor that directly measures the amount of the liquid, instead of detecting the liquid surface of the fuel or the urea water, like the liquid surface detection sensors 39F and 39A.

Further, the engine controller 30 transmits a "signal indicating that the engine 31 is during an operation" to the monitor 20 through the in-vehicle signal line L, and an operation time measurement unit 24 of the monitor 20 counts a time in which the signal is being received, and obtains an operation time. Note that the engine controller 30 receives a signal from the rotation speed detection sensor 38 that detects the rotation speed of the engine 31, generates the "signal indicating that the engine 31 is during an operation," and transmits the signal to the monitor 20. Even if the "the signal indicating that the engine 31 is during an operation" is not transmitted from the engine controller 30 to the monitor 20 for some reason, the operation time can be obtained in the following manner. A signal (predetermined voltage) is transmitted from the alternator 35 to the monitor 20 through a signal line 35A. The operation time measurement unit 24 of the monitor 20 counts a time in which the signal (hereinafter, an alternator signal) is being received from the alternator 35, and can obtain the operation time.

A traveling device 43 causes the working vehicle 1 to travel by power generated by the engine 31. The traveling device 43 includes a hydraulic motor (not illustrated) and a crawler belt 43C. The hydraulic motor (not illustrated) in the traveling device 43 is rotated by hydraulic oil supplied from the hydraulic pump 32 driven by the engine 31. The hydraulic motor (not illustrated) rotates the crawler belt 43C, so that the working vehicle 1 travels. In the hydraulic pump 32, a swash plate angle is controlled by the pump controller 50, and a discharge amount of hydraulic oil supplied to a hydraulic cylinder (not illustrated) of a working machine or the like is controlled.

The working vehicle 1 includes the storage battery 44. The storage battery 44 is a secondary battery, such as a lead storage battery or a nickel-hydrogen storage battery. The storage battery 44 supplies the power to the starter 51 for starting the engine 31, and supplies the power to various electronic devices including the processing device 10 provided in the working vehicle 1. The storage battery 44 is charged by the power supplied from the alternator 35. The alternator 35 generates the power by being driven in conjunction with driving of the engine 31. The power generated by the alternator 35 is charged in the storage battery 44.

As described above, the alternator signal indicating that the power is generated by the alternator 35 is transmitted to the monitor 20 through the signal line 35A. By receiving the alternator signal, the monitor 20 can determine whether the alternator 35 is normally operated. Note that the monitor 20 may obtain the operation time of the working vehicle 1 by counting the time in which the alternator signal is being received on a steady basis, instead of using the "signal indicating that the engine 31 is during an operation" as described above.

The power supplied from the storage battery 44 is supplied to the electronic devices, such as the starter 51, the pump controller 50, the engine controller 30, the processing device 10, and the monitor 20, through the key switch 46, for example. The key switch 46 is electrically connected to the storage battery 44, and is further electrically connected to the pump controller 50, the engine controller 30, the processing device 10, and the monitor 20. As the key switch 46, a key switch using a cylinder lock, a push-button type key switch, an immobilizer key using wireless communication, or the like can be used. When the key switch 46 is turned ON, the power is supplied from the storage battery 44 to the pump controller 50, the engine controller 30, the processing device 10, and the monitor 20. When the key switch 46 is turned OFF, the power from the storage battery 44 to the pump controller 50, the engine controller 30, the processing device 10, and the monitor 20 is cut off.

The processing device 10 includes a processing unit 11, a storage unit 12 and an input/output unit 13. The processing device 10 controls the working vehicle 1, generates abnormal information, and collects operation information. The processing device 10 transmits the generated abnormal information and operation information to an outside of the working vehicle 1 through a communication device 14 and an antenna 14A, for example.

The operation information includes information obtained from various sensors, such as a pressure sensor (not illustrated), the rotation speed detection sensor 38, a temperature sensor and the liquid surface detection sensors 39A and 39F. An example of the information obtained from the pressure sensor includes an oil pressure of engine oil. Further, an example of the information obtained from the rotation speed detection sensor 38 includes a rotation speed of the engine 31, and an example of the information obtained from the temperature sensor includes a temperature of cooling water of the engine 31. Position information of the working vehicle 1 detected by a position detection device 15 and information related to abnormality having occurred in the working vehicle 1 are also included in the operation information. The information related to abnormality having occurred in the working vehicle 1 is, for example, a certain error code, a type of the abnormality, or an occurrence time of the abnormality. The operation information is not limited to the information related to the abnormality having occurred in the working vehicle 1, and may include information indicating that the working vehicle 1 is normally operated, like the operation time.

The processing unit 11 generates the operation information. Further, the processing unit 11 includes a unit urea water consumption amount calculation unit 11A, a urea water remaining time calculation unit 11B, and an output processing unit 11C. The unit urea water consumption amount calculation unit 11A calculates a unit urea water consumption amount for each predetermined unit operation time based on the urea water residual amount detected by the urea water residual amount detection unit 23 described above. The urea water remaining time calculation unit 11B calculates an average urea water consumption amount based on a unit urea water consumption amount within a past predetermined operation time, excluding a unit urea water consumption amount calculated at the time of occurrence of a specific phenomenon of the unit urea water consumption amount calculated by the unit urea water consumption amount calculation unit 11A, and calculates a urea water remaining time to an output restriction start time based on the average urea water consumption amount and a current urea water residual amount. The output processing unit 11C outputs guidance of the urea water remaining time calculated by the urea water remaining time calculation unit 11B to the monitor 20. Details of processing performed by the unit urea water consumption amount calculation unit 11A, the urea water remaining time calculation unit 11B, and the output processing unit 11C will be described below. Note that the specific phenomenon is one of discharge of the urea water from the urea water tank 42, supply of the urea water to the urea water tank 42, and system abnormality. The discharge of the urea water from the urea water tank 42 is to operate a drain valve (not illustrated) and discharge the urea water from the urea water tank 42 when the urea water is supposed to be frozen due to a low outdoor temperature or when the urea water remained in the urea water tank 42 is replaced. The system abnormality is a case in which abnormality has occurred in the temperature sensor, or the like included in the exhaust gas processing device 40, for example, or a case in which communication abnormality has occurred in the in-vehicle signal line L.

The input/output unit 13 is an interface that electrically connects an inside of the processing device 10 and the in-vehicle signal line L. The in-vehicle signal line L is a controller area network (CAN), for example. A terminal LT is electrically connected to the in-vehicle signal line L. By connection of a terminal device, and the like to the terminal LT, the terminal device, the processing device 10, and the like can mutually exchange information through the terminal LT and the in-vehicle signal line L.

The communication device 14 includes the antenna 14A. The communication device 14 is used when the processing device 10 communicates with an outside of the working vehicle 1. The position detection device 15 includes a GPS antenna 15A. The position detection device 15 converts a radio wave received by the GPS antenna 15A into an electrical signal, and obtains position information of the working vehicle 1.

The monitor 20 is a display device that includes a display unit 21 that displays various types of information of the working vehicle 1, an input unit 22 that inputs various types of information, the above-described urea water residual amount detection unit 23, and the above-described operation time measurement unit 24. Note that the urea water residual amount detection unit 23, the operation time measurement unit 24, the unit urea water consumption amount calculation unit 11A, the urea water remaining time calculation unit 11B, the output processing unit 11C, the urea water residual amount detection unit 23, the operation time measurement unit 24 and the display unit 21 compose a urea water supply guidance output device. Note that the processing, such as calculation, executed by the urea water residual amount detection unit 23 and the operation time measurement unit 24 may be performed by another controller, or the like. Further, the input unit 22 may be a separate body from the monitor 20, and the input unit 22 may be provided in a console inside a driver's cab (not illustrated).

(Output of Urea Water Supply Guidance)

Figure 2:
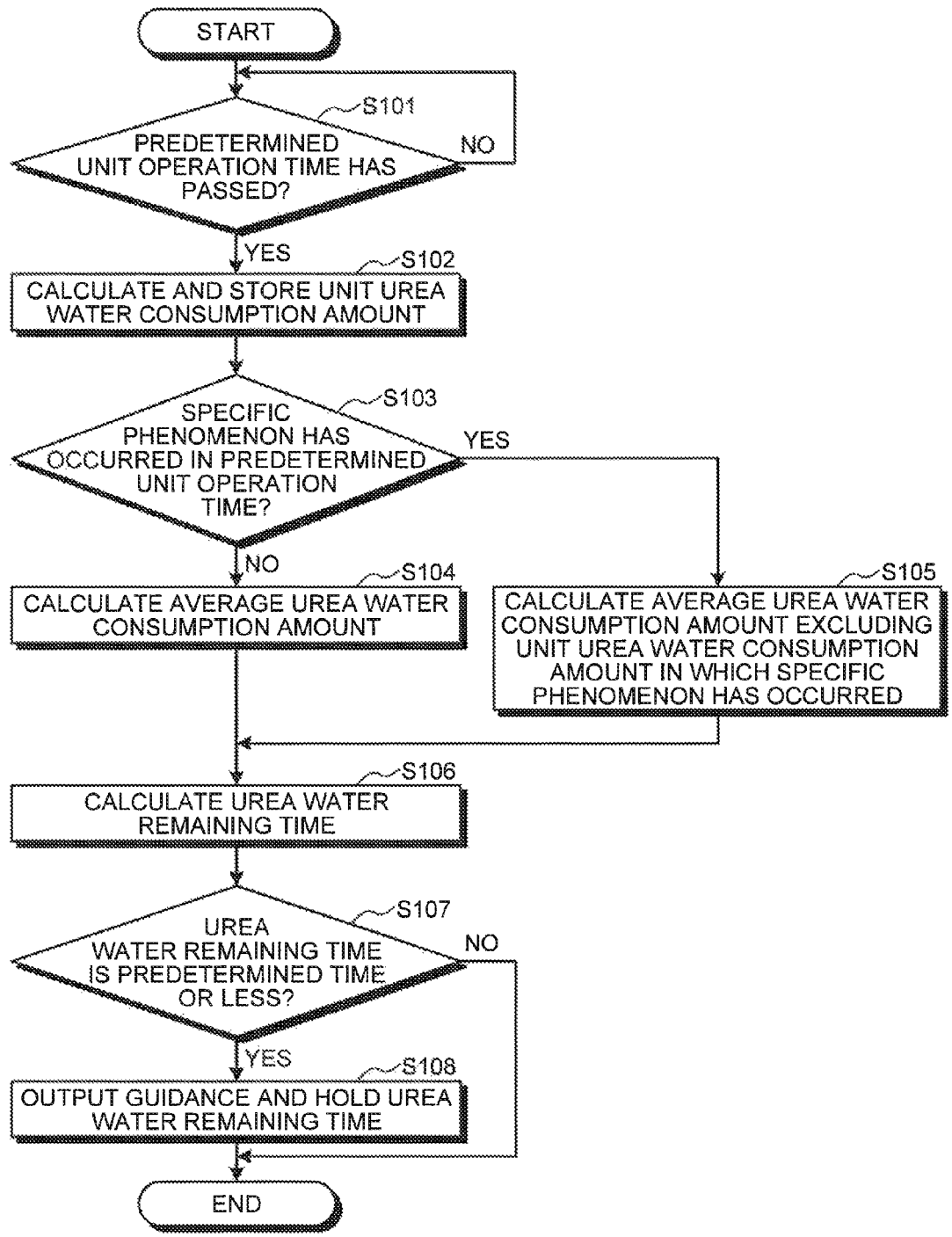
FIG. 2 is a flowchart illustrating a procedure of outputting urea water supply guidance by a processing unit.
Figure 3:
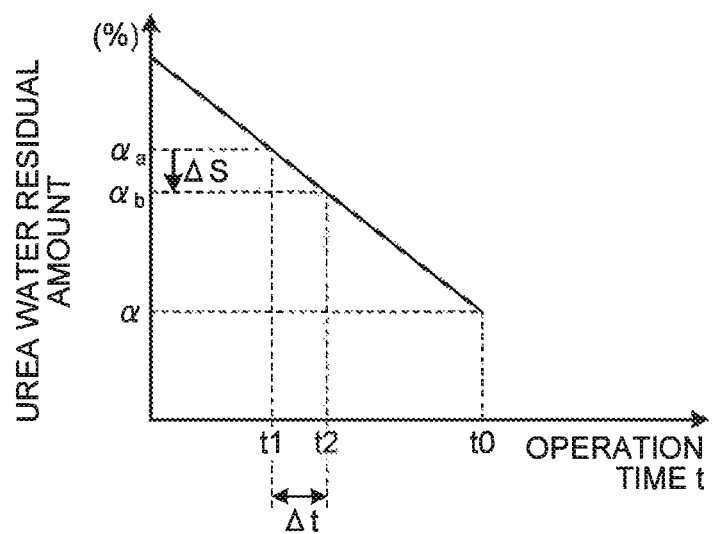
FIG. 3 is an explanatory diagram describing calculation of a unit urea water consumption amount by a unit urea water consumption amount calculation unit.

Next, a procedure of outputting urea water supply guidance by the processing unit 11 will be described with reference to the flowchart illustrated in FIG. 2. First, the unit urea water consumption amount calculation unit 11A determines whether the operation time measured by the operation time measurement unit 24 has passed a predetermined unit operation time $\Delta t$, for example, whether the operation time has passed one hour (step S101). When the operation time has not passed the predetermined unit operation time (No in step S101), the unit urea water consumption amount calculation unit 11A repeats the determination processing of step S101. Meanwhile, when the operation time has passed the predetermined unit operation time (Yes in step S101), the unit urea water consumption amount calculation unit 11A calculates the unit urea water consumption amount for each predetermined unit operation time based on the urea water residual amount detected by the urea water residual amount detection unit 23, and holds the unit urea water consumption amount in the storage unit 12 (step S102).

Figures 1, 4:
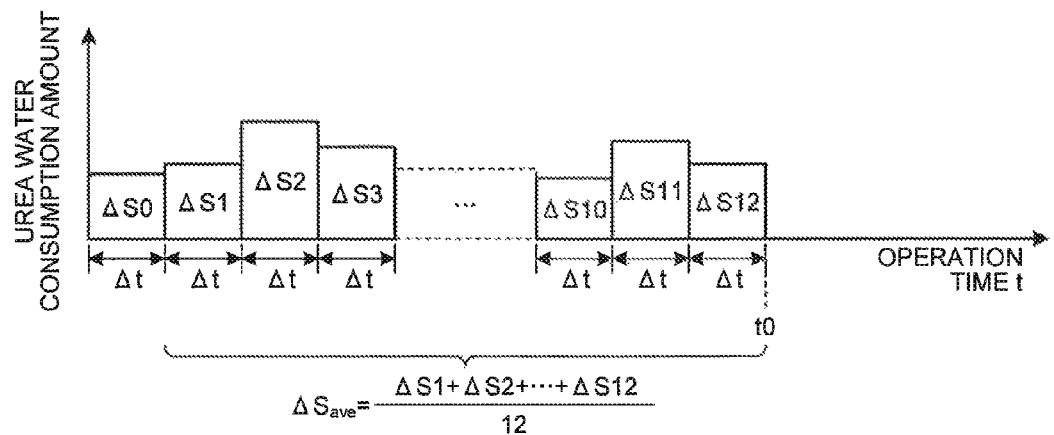
Figures 2, 4:
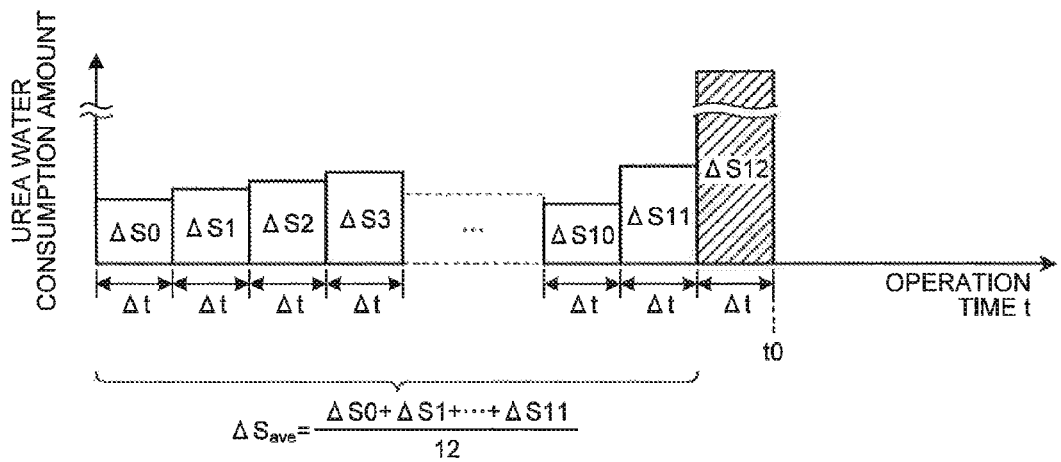

To be specific, the unit urea water consumption amount calculation unit 11A calculates, as a unit urea water consumption amount $\Delta S$, a consumption amount (decreased amount) $\Delta S$ $(=\Delta a - \Delta b)$ of a urea water residual amount $\alpha$ in the predetermined unit operation time $\Delta t$ every time the predetermined unit operation time $\Delta t$ has passed. Then, the unit urea water consumption amounts $\Delta S$ are sequentially held in the storage unit 12 in time series as unit urea water consumption amounts $\Delta S0$ to $\Delta S12$ as the predetermined unit operation time $\Delta t$ passes, as illustrated in FIG. 4-1, for example. Up to 12 unit urea water consumption amounts $\Delta S$ are stored in the storage unit 12. Therefore, in the case of FIG. 4-1, when the unit urea water consumption amount $\Delta S12$ is obtained, the unit urea water consumption amount $\Delta S0$ is deleted.

Following that, the urea water remaining time calculation unit 11B determines whether the specific phenomenon has occurred in a predetermined unit operation time $\Delta t$ (step S103). When the specific phenomenon has not occurred in the predetermined unit operation time $\Delta t$ (No in step S103), the urea water remaining time calculation unit 11B calculates an average urea water consumption amount $\Delta Save$ that is an average value of the past 12 unit urea water consumption amounts $\Delta S$ (step S104). For example, as illustrated in FIG. 4-1, the urea water remaining time calculation unit 11B adds the 12 unit urea water consumption amounts $\Delta S1$ to $\Delta S12$ in a predetermined operation time from a current timing t0 (12 hours), and calculates a value obtained by dividing the addition result by 12 as the average urea water consumption amount ΔSave.

Meanwhile, when the specific phenomenon has occurred in the predetermined unit operation time Δt (Yes in step S103), the urea water remaining time calculation unit 11B calculates the average urea water consumption amount ΔSave that is an average value of the obtained unit urea water consumption amounts ΔS, excluding the unit urea water consumption amount ΔS in which the specific phenomenon has occurred (step S105). For example, as illustrated in FIG. 4-2, when the specific phenomenon has occurred in a period (predetermined unit operation time Δt) in which the unit urea water consumption amount ΔS12 is calculated, the urea water remaining time calculation unit 11B excludes the unit urea water consumption amount ΔS12 and adds 12 unit urea water consumption amounts ΔS0 to ΔS11 obtained in the predetermined operation time (12 hours) from the current timing t0 to one hour (Δt hour) prior to the current timing t0, and calculates a value obtained by dividing the addition result by 12 as the average urea water consumption amount ΔSave.

Further, as described above, the specific phenomenon is one of discharge of the urea water from the urea water tank 42, supply of the urea water to the urea water tank 42, and system abnormality. The case in which the specific phenomenon is determined to be the discharge of the urea water (Yes in step S103) is a case in which the unit urea water consumption amount ΔS is changed (consumed) by a predetermined percentage (%) or more to a full urea water amount. The predetermined percentage (%) is a value set in consideration of a value larger than the urea water (unit urea water consumption amount ΔS) consumed when a usual operation is performed without occurrence of the specific phenomenon in the working vehicle 1. When the unit urea water consumption amount ΔS is changed by the predetermined percentage (%) or more, it is inappropriate to include an average urea water consumption amount Δ thereof as an object to be calculated for obtaining the average urea water consumption amount ΔSave. Further, the case in which the specific phenomenon is determined to be the supply of the urea water (Yes in step S103) is a case in which the value of the unit urea water consumption amount ΔS (=Δa−Δb) becomes a minus value. When the unit urea water consumption amount ΔS becomes a minus value, it is inappropriate to include the unit urea water consumption amount ΔS as the object to be calculated of the average urea water consumption amount ΔSave. Whether the system abnormality has occurred as the specific phenomenon can be determined such that the urea water remaining time calculation unit 11B receives the signal that indicates occurrence of the abnormality from the engine controller 30 when the abnormality has occurred in the temperature sensor included in the exhaust gas processing device 40. Even if the unit urea water consumption amount calculation unit 11A obtains the unit urea water consumption amount ΔS in a state where such a specific phenomenon has occurred (Yes in step S103), the urea water remaining time calculation unit 11B obtains the average urea water consumption amount ΔSave, excluding the unit urea water consumption amount ΔS. The reason why the unit urea water consumption amount ΔS is not included in calculation of the urea water consumption amount in the case where the system abnormality has occurred is that data of when the system abnormality has occurred is not reliable.

Note that the 12 unit urea water consumption amounts Δ are used in the calculation of the average urea water consumption amount ΔSave. The times of the 12 unit urea water consumption amounts Δ correspond to 12 hours. The reason why the operation time of the 12 hours is used as the time of the calculation of the average urea water consumption amount ΔSave is as follows. Typically, the operation time per day of a working vehicle is eight hours on average. A more accurate average urea water consumption amount ΔSave can be obtained by using more unit urea water consumption amounts ΔS, rather than obtaining the average urea water consumption amount ΔSave within the eight hours. Therefore, a more reliable average urea water consumption amount ΔSave can be obtained by the eight hours plus another four hours, that is, by the unit urea water consumption amounts ΔS of 12 hours as a total. Note that the time setting in which a condition at the calculation of the average urea water consumption amount ΔSave is 12 hours can be changed using the input unit 22 of the monitor 20.

Following that, the urea water remaining time calculation unit 11B calculates a urea water remaining time ΔT that indicates a time to the generation of the urea water supply alarm or the output restriction start time based on the average urea water consumption amount ΔSave calculated in step S104 or S105 and the current urea water residual amount α (step S106). To be specific, the urea water remaining time ΔT is calculated as:

$$\Delta T\,[h] = (\alpha\,[\%] - 2.5\,[\%]) / (\Delta Save\,[\%/h] * 1.15\,[\%/h])$$

Note that a numerical value of 2.5 [%] is a rate (setting value) set as the urea water residual amount at the generation of the urea water supply alarm or an output restriction start time of the engine, or the like. Therefore, 2.5 [%] may be another setting value. Further, 1.15 [%/h] is a safety factor, and is added in consideration of variation of the average urea water consumption amount ΔSave. This 1.15 [%/h] may also be another setting value because this value determines magnitude of the safety factor.

Following that, the output processing unit 11C determines whether the urea water remaining time ΔT calculated by the urea water remaining time calculation unit 11B is a predetermined time or less (step S107). When the urea water remaining time ΔT is the predetermined time or less (Yes in step S107), the output processing unit 11C outputs an instruction for outputting guidance including the urea water remaining time ΔT to the monitor 20, holds the urea water remaining time ΔT in the storage unit 12 (step S108), and terminates the processing, for example. Meanwhile, when the urea water remaining time ΔT is not the predetermined time or less (No in step S107), the output processing unit 11C terminates the processing as it is. By an output of guidance of the information related to the urea water supply including the urea water remaining time ΔT that indicates the time to the generation of the urea water supply alarm or the output restriction start time, the operator can accurately and reliably recognize the information related to the urea water supply. Note that the above-described processing is repeatedly performed at each predetermined timing. Details of the predetermined timing will be described below.

(Output of Guidance of Urea Water Supply at Key-on Time)

Figure 5:
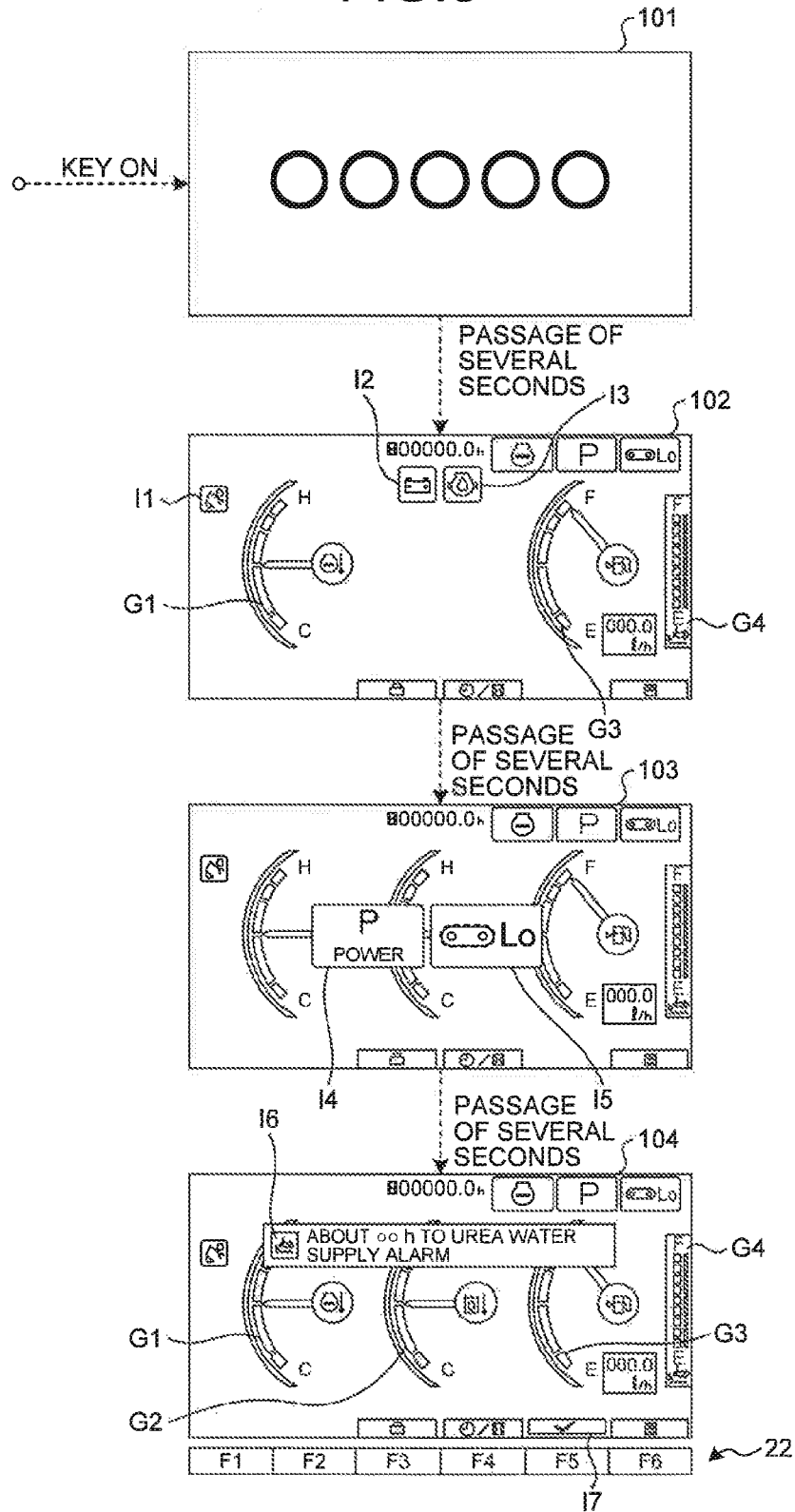
FIG. 5 is a screen transition diagram illustrating an example of an output of urea water supply guidance on a display screen at a key-on time.

FIG. 5 is a screen transition diagram of the display unit 21 of the monitor 20 of when the operator of the working vehicle 1 or the like operates the key switch 46 to turn key-on. That is, FIG. 5 is a screen transition diagram indicating an example of outputting guidance of urea water supply using the display unit 21. As illustrated in FIG. 5, when the key switch 46 is turned on, an initial screen 101 indicating "during running," and the like are displayed in the display unit 21. The initial screen 101 may be caused not to be displayed. After passage of several seconds, a start-up check display screen 102 that displays icons I1 to I3 is displayed on the display screen in order to cause the operator to recognize types and display positions of the icons I1 to I3 displayed when failure occurs. Further, after passage of several seconds, an initial mode display screen 103 on which a working mode icon I4 and a traveling mode icon I5 are displayed in the center of the display screen in yellow is displayed. In FIG. 5, the working mode is set to "P (power mode)," and the traveling mode is set to "Lo (low-speed mode)." After passage of several seconds, a urea water supply guidance icon I6 is displayed in an upper portion of a final start-up check display screen 104.

A message in the urea water supply guidance icon I6 is a message that notifies a time at which alarm of "about oo h to the urea water supply alarm" is generated when the urea water remaining time $\Delta T$ is, for example, from one hour to eight hours, both inclusive, as illustrated in FIG. 5, and is a message that notifies the fact that a time at which urea water supply alarm is generated is soon, indicating "a little time left to the urea water supply alarm," when the urea water remaining time $\Delta T$ is less than one hour. Note that the derate control that is the output restriction control of the engine 31, and the like, may be executed, as described above, at the same timing as the urea water supply alarm is generated.

Further, the urea water supply guidance icon I6 may be displayed on the start-up check display screen 104 with the understanding that the urea water remaining time $\Delta T$ does not mean the time of the generation of urea water supply alarm, but the urea water remaining time $\Delta T$ means a time at which the derate control that is the output restriction control of the engine 31, and the like is executed. That is, the fact that the derate control of the engine 31, and the like is to be executed is notified to the operator if the operator operates the working vehicle 1 without supplying the urea water. Alternatively, the urea water supply guidance icon I6 may be displayed on the start-up check display screen 104 with the understanding that the urea water remaining time $\Delta T$ means a time at which both of the generation of urea water supply alarm and the derate control that is the output restriction control of the engine 31, and the like are executed.

Note that, when the urea water supply guidance icon I6 is not displayed, the urea water remaining time $\Delta T$ held in the storage unit 12 exceeds eight hours. When the urea water remaining time $\Delta T$ is eight hours or less, other than the key-on time, the urea water supply guidance icon I6 is displayed on the display screen at that point. The reason why a threshold of the display of the urea water remaining time $\Delta T$ is eight hours is that eight hours is regarded as the working time of one day using the working vehicle 1. That is, when it is the urea water remaining time $\Delta T$ that exceeds eight hours at the key-on time, it is not necessary to perform the urea water supply on the day at which the key-on is performed, and thus the urea water supply guidance icon I6 is not displayed. In contrast, when the urea water remaining time $\Delta T$ is within eight hours at the key-on time, there is a possibility that the urea water supply is performed during work on the day at which the key-on is performed. Therefore, the urea water supply guidance icon I6 is displayed at the key-on time, and attracts attention. Therefore, with display or non-display of the urea water supply guidance icon I6 in the display unit 21, the arrangement of urea water or the urea water supply can be urged before the start of work, the working plan can be appropriately made, and the work may not be interrupted.

After passage of a predetermined time, the urea water supply guidance icon I6 disappears from the display screen of the display unit 21. Further, function switches F1 to F6 as the input unit 22 are arranged in a lower portion of the display screen, and a guidance icon, for example, a guidance icon I7 is displayed as needed at a lower position of the display screen above and corresponding to each of the function switches F1 to F6. When the urea water supply guidance icon I6 is displayed on the start-up check display screen 104, the guidance icon I7 is displayed at a position corresponding to the function switch F5. The guidance icon I7 is an icon that indicates a location of a function key that is pressed for instructing non-display of the urea water supply guidance icon I6. By a press of the function key F5, the non-display of the urea water supply guidance icon I6 is selected, and the urea water supply guidance icon I6 disappears from the start-up check display screen 104. Therefore, by the press of the function key F5, the urea water supply guidance icon I6 can be made to non-display even if a predetermined time has not been passed. It is favorable to sound a buzzer (not illustrated), or the like, when the urea water supply guidance icon I6 is displayed. Alternatively, the contents displayed in the urea water supply guidance icon I6 may be output as a sound using a speaker (not illustrated), or the like. Further, with a press of a specific key or a guidance icon, the urea water supply guidance icon I6 may be able to be displayed at any time. For example, the guidance icon I7 for re-displaying the urea water supply guidance icon I6 is displayed, and by a press of the function key F5 corresponding to the guidance icon I7, the display of the urea water supply guidance icon I6 may be selected.

Note that, on the start-up check display screen 104 of FIG. 5, an engine water temperature gauge G1 that indicates the water temperature of the cooling water of the engine, a hydraulic oil temperature gauge G2 that indicates the oil temperature of the hydraulic oil in a hydraulic circuit, and a fuel level gauge G3 that indicates a level of the residual amount of the fuel are displayed in the center of the screen side by side. Note that the hydraulic oil temperature gauge G2 may not be displayed on the start-up check display screen 104 or another display screen. Indicators of the gauges G1 to G3 deflect based on detection signals of corresponding sensors. Further, a urea water level gauge G4 that indicates a level of the residual amount of the urea water in a bar manner is displayed at a right side of the initial display screen 104 and next to the fuel level gauge G3.

Figure 6:
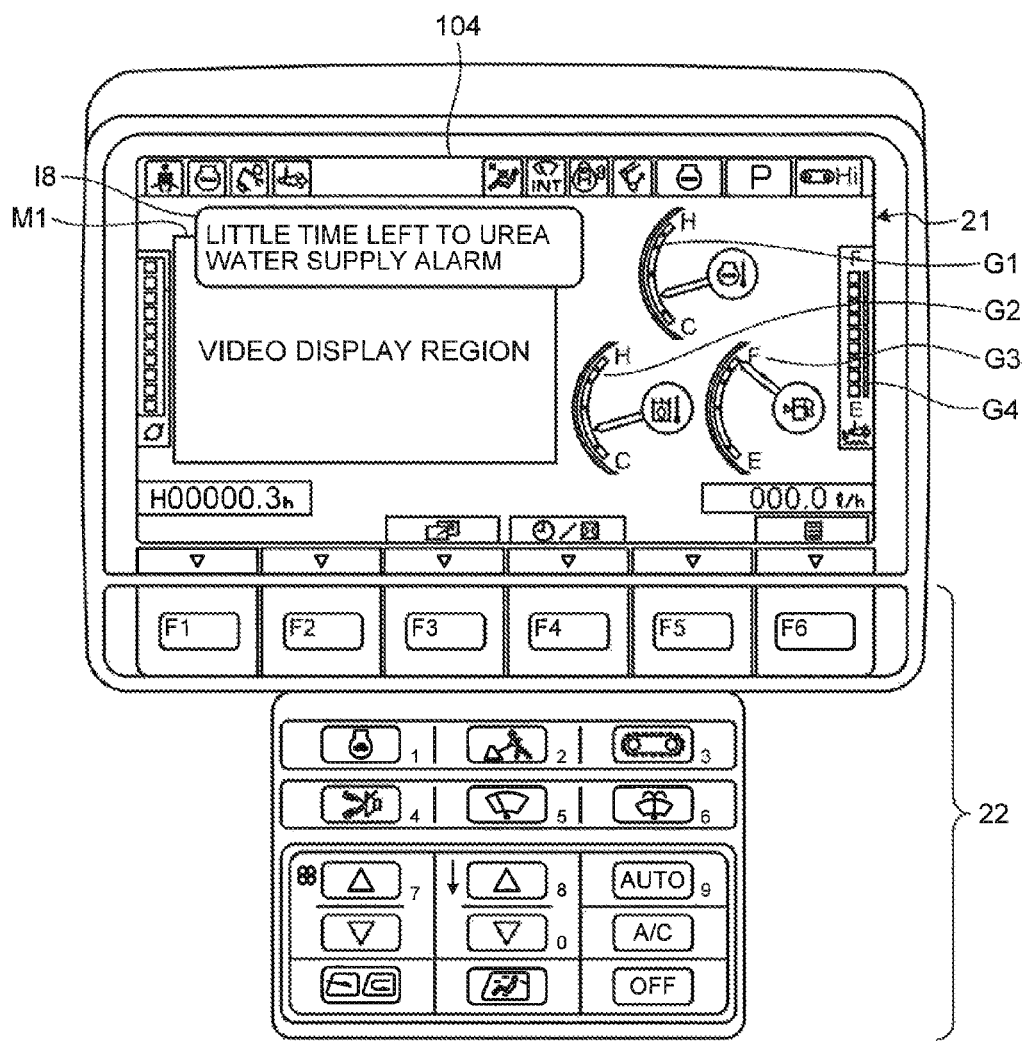
FIG. 6 is a diagram illustrating an example of an arrangement of urea water supply guidance icons of when a video display region M1 is provided in a left region of a start-up check display screen.

Here, when the working vehicle 1 mounts a rear camera on an upper portion of a counterweight, for example, a video display region M1 is provided in a portion of the start-up check display screen 104, for example, in a left region, as illustrated in FIG. 6. A video imaged by the rear camera is displayed in the video display region M1. Further, the engine water temperature gauge G1, the hydraulic oil temperature gauge G2 and the fuel level gauge G3 are displayed in a right region of the start-up check display screen 104 in a triangle manner. In this case, the hydraulic oil temperature gauge G2 may not be displayed on the start-up check display screen 104.

On the display screen where the video display region M1 is displayed in the display unit 21, as illustrated in FIG. 6, a urea water supply guidance icon I8 corresponding to the urea water supply guidance icon I6 is displayed in an upper peripheral portion of the video display region M1.

Note that some working vehicles include an energy saving guidance output function. The energy saving guidance output function is to display ecological guidance that indicates a fact that a fuel consumption deterioration drive operation is performed or one-point guidance for urging improvement of the fuel consumption deterioration drive operation by an energy saving guidance icon, for example, when the fuel consumption deterioration drive operation is performed. Examples of the fuel consumption deterioration drive operation include a drive operation in which long time idling is performed, a drive operation in which oil pressure relief is continued, and a drive operation in which driving that can be executed in an energy saving mode is executed in another high energy mode. In a working vehicle that has the energy saving guidance output function, the urea water supply guidance icons I6 and I8 are preferentially displayed to the energy saving guidance icon after the key-on is performed. That is, the urea water supply guidance icons I6 and I8 are preferentially displayed to the energy saving guidance icon.

Further, in the above-described embodiment, the unit urea water consumption amount calculation unit 11A, the urea water remaining time calculation unit 11B, and the output processing unit 11C may be provided in the monitor 20, the engine controller 30, or the like connected to the in-vehicle signal line L, other than the processing device 10. Similarly, the urea water residual amount detection unit 23 and the operation time measurement unit 24 may be provided in the processing device 10, the engine controller 30, or the like connected to the in-vehicle signal line L, other than the monitor 20.

REFERENCE SIGNS LIST

1 Working vehicle
10 Processing device
11 Processing unit
11A Unit urea water consumption amount calculation unit
11B Urea water remaining time calculation unit
11C Output processing unit
12 Storage unit
13 Input/output unit
14 Communication device
14A Antenna
15 Position detection device
15A GPS antenna
20 Monitor
21 Display unit
22 Input unit
23 Urea water residual amount detection unit
24 Operation time measurement unit
30 Engine controller
30S Fuel adjustment dial
31 Engine
32 Hydraulic pump
35 Alternator
35A Signal line
38 Rotation speed detection sensor
39F Liquid surface detection sensor
39A Liquid surface detection sensor
40 Exhaust gas processing device
41 Fuel tank
42 Urea water tank
43 Traveling device
43C Crawler belt
44 Storage battery
46 Key switch
50 Pump controller
51 Starter
104 Start-up check display screen
F1 to F6 Function switch
G1 Engine water temperature gauge
G2 Hydraulic oil temperature gauge
G3 Fuel level gauge
G4 Urea water level gauge
I4 Working mode icon
I5 Traveling mode icon
I6 and I8 Urea water supply guidance icon
I7 Guidance icon
L In-vehicle signal line
M1 Video display region
$\alpha$ Urea water residual amount
$\Delta S$, and $\Delta S0$ to $\Delta S12$ Unit urea water consumption amount
$\Delta Save$ Average urea water consumption amount
$\Delta T$ Urea water remaining time
$\Delta t$ Predetermined unit operation time

The invention claimed is:

1. A urea water supply guidance output device for a working vehicle configured to perform exhaust gas processing using urea water in a urea water tank, comprising:
a urea water residual amount detection unit configured to detect a urea water residual amount in the urea water tank;
an operation time measurement unit configured to measure an operation time of the working vehicle;
a unit urea water consumption amount calculation unit configured to calculate a unit urea water consumption amount for each predetermined unit operation time based on the urea water residual amount;
a urea water remaining time calculation unit configured to calculate an average urea water consumption amount based on a unit urea water consumption amount in a past predetermined operation time, excluding a unit urea water consumption amount calculated at an occurrence of a specific phenomenon of the unit urea water consumption amount, and to calculate a urea water remaining time indicating a time to generation of a urea water supply alarm based on the average urea water consumption amount and a current urea water residual amount; and
an output processing unit configured to output guidance including the urea water remaining time when the urea water remaining time is a predetermined time or less,
wherein output restriction control of the working vehicle is performed according to the urea water remaining time.

2. The urea water supply guidance output device for a working vehicle according to claim 1, wherein the specific phenomenon is one of discharge of the urea water from the urea water tank, supply of the urea water to the urea water tank, and system abnormality.

3. The urea water supply guidance output device for a working vehicle according to claim 1, wherein the urea water remaining time is a time to execution of output restriction control of the working vehicle.

4. The urea water supply guidance output device for a working vehicle according to claim 1, comprising an input unit configured to input an instruction of non-display or re-display of the output of guidance of the urea water remaining time.

5. The urea water supply guidance output device for a working vehicle according to claim 1, wherein the output processing unit is configured to output the output of guidance including the urea water remaining time after key-on is performed.

6. A urea water supply guidance output device for a working vehicle configured to perform exhaust gas processing using urea water in a urea water tank, the device comprising:
- a urea water residual amount detection unit configured to detect a urea water residual amount in the urea water tank;
- an operation time measurement unit configured to measure an operation time of the working vehicle;
- a unit urea water consumption amount calculation unit configured to calculate a unit urea water consumption amount for each predetermined unit operation time based on the urea water residual amount;
- a urea water remaining time calculation unit configured to calculate an average urea water consumption amount based on a unit urea water consumption amount in a past predetermined operation time, excluding a unit urea water consumption amount calculated at an occurrence of a specific phenomenon of one of discharge of the urea water from the urea water tank, supply of the urea water to the urea water tank, and system abnormality, of the unit urea water consumption amount, and to calculate a urea water remaining time indicating a time to generation of a urea water supply alarm based on the average urea water consumption amount and a current urea water residual amount; and
- an output processing unit configured to output guidance including the urea water remaining time at least after key-on is performed when the urea water remaining time is a predetermined time or less,
- wherein output restriction control of the working vehicle is performed according to the urea water remaining time.

7. A method of outputting guidance of urea water supply for a working vehicle configured to perform exhaust gas processing using urea water in a urea water tank, the method comprising:
- detecting a urea water residual amount in the urea water tank;
- measuring an operation time of the working vehicle;
- calculating a unit urea water consumption amount for each predetermined unit operation time based on the urea water residual amount;
- calculating an average urea water consumption amount based on a unit urea water consumption amount in a past predetermined operation time, excluding a unit urea water consumption amount calculated at an occurrence of a specific phenomenon of the unit urea water consumption amount, and calculating a urea water remaining time indicating a time to generation of a urea water supply alarm based on the average urea water consumption amount and a current urea water residual amount;
- outputting guidance including the urea water remaining time when the urea water remaining time is a predetermined time or less; and
- performing output restriction control of the working vehicle according to the urea water remaining time.

8. The method of outputting guidance of urea water supply for a working vehicle according to claim 7, wherein the specific phenomenon is one of discharge of the urea water from the urea water tank, supply of the urea water to the urea water tank, and system abnormality.

9. The method of outputting guidance of urea water supply for a working vehicle according to claim 7, wherein the urea water remaining time is a time to execution of output restriction control of the working vehicle.

* * * * *